United States Patent [19]

Cho et al.

[11] Patent Number: 4,940,547
[45] Date of Patent: Jul. 10, 1990

[54] USE OF INHIBITORY SOLVENTS IN MULTI-MEMBRANE BIOREACTOR

[75] Inventors: Toohyon Cho; Michael L. Shuler, both of Ithaca, N.Y.

[73] Assignee: Cornell Research Foundation, Inc., Ithaca, N.Y.

[21] Appl. No.: 882,803

[22] Filed: Jul. 7, 1986

[51] Int. Cl.$^5$ .............................................. B01D 13/00
[52] U.S. Cl. ...................................... 210/643; 435/161
[58] Field of Search ................ 435/161, 813; 210/638, 210/643, 644, 500.23

[56] References Cited

U.S. PATENT DOCUMENTS 3,956,112  5/1976  Lee et al. ............................ 210/644
4,442,206  4/1984  Michaels et al. ............... 435/161 X

OTHER PUBLICATIONS

Roddy, 1981, Ind. Eng. Chem. Process Des. Dev., 20:104–108.
Matsumura et al., 3rd European Congress Biotechnol., 2:415–423.
Slapack et al., "Thermophilic Microbes in Ethanol Production", CRC Press Inc., Boco Raton, Fla., 1985, p. 135.
Hahn-Hagerdal et al., 1981, Biotechnol. Bioeng. Sympos., 11:651–661.
Margaritis et al., 1978, Biotechnol. Bioeng., 20:727–753.
Margaritis et al., 1978, Biotechnol. Bioeng., 20:727–753.
Kyung et al., 1984, Biotechnol. Bioeng., 26:252–256.
Murphy et al., Process Biotechnol., Nov./Dec. 1982.
Minier et al., 1982, Biotechnol. Bioeng., 24:1565–1579.
Brown et al., 1981, Euro. J. Appl. Microbiol. Biotechnol., 11:151–155.
Ghose et al., 1979, Biotechnol. Bioeng., 27:1401–1420.
Luong, 1985, Biotechnol. Bioeng., 27:280–285.
Aiba et al., 1968, Biotechnol. Bioeng., 10:845–865.
Holzberg et al., 1967, Biotechnol. Bioeng., 9:413–427.
Wang et al., 1981, Biotechnol. Bioeng. Sympo., 11:555–565.

*Primary Examiner*—Frank Spear
*Attorney, Agent, or Firm*—Jones, Tullar & Cooper

[57] ABSTRACT

An immobilized liquid membrane is employed to allow use of a product-extracting solvent which is normally toxic toward a cell layer which produces the product in a membrane-moderated biological reaction.

5 Claims, 6 Drawing Sheets

USE OF INHIBITORY SOLVENTS IN MULTI-MEMBRANE BIOREACTOR

BACKGROUND OF THE INVENTION

This invention was made in part under NASA subcontract Grant No. 957240 and NSF Grant No. CPE-8114995. The U.S. Government has certain rights to this invention.

Bioreactor studies have increasingly focused on immobilized cell systems [Chibata et al., *Ann. Rev. Biophys. Bioeng.*, 1981, 10:197; Margaritis et al., *CRC Crit. Rev. Biotechnical*, 1:339 (1981): Inloes, "Immobilization of Bacterial and Yeast Cells in Hollow-Fiber Membrane Bioreactors", 1982, Ph.D. Thesis, Stanford University: Nagashima et al., *Biotechnol. Bioeng.*, 26:992 (1984)]. Possible improvements in productivity due to high cell densities has been a motivating factor. However, cell immobilization may not give increases of productivity in some systems due to feedback inhibition. In these cases integration of production and recovery in the same unit may be advantageous. The integration of bioconversion and separation to improve the productivity of a bioreactor has been considered, [Wang, *Ann. NY Acad. Sci.*, p. 313 (1983): Kominek, *Antimicrob. Agents Chemother.*, 7:856 and 861 (1975); Finn, *J. Ferm. Technol.*, 44:305 (1966)], although few of these studies have focused on immobilized microbes. Since downstream product recovery is often a significant cost (both in money and energy), the challenge comes from not only the improvement of productivity in the bioreactor but also to reduce downstream processing costs.

A purpose of this invention is an immobilized cell bioreactor in which production and recovery can be integrated, and in which a solvent otherwise deliterious to the system can be used to recover product. The process is exemplified by ethanol production from glucose using *Saccharomyces cerevisiae*. This system provides a good model since it has been extensively studied in a variety of other reactors, and the effects of feedback inhibition are well known, [Brown et al., *Euro. J. Appl. Microbiol. Biotechnol.*, 11:151 (1981); Ghose et al., *Biotechnol. Bioeng.*, 21:1401 (1979); Luong, *Biotechnol. Bioeng.*, 27:280 (1985); Aiba et al., *Biotechnol. Bioeng.*, 10:845 (1968); Holzberg et al., *Biotechnol. Bioeng.*, 9:413 (1967)].

Several reactor configurations for the simultaneous formation of ethanol and its release from the broth have been advocated. Among these are vacuum fermentation [Ramalingam, "Vacuum Alcohol Fermentation," 1975, Ph.D. Thesis, Cornell University], evaporative fermentation [Dale et al., *Biotechnol. Bioeng.*, 27:932 and 943 (1985)], adsorption onto activated carbon [Wang et al., *Biotechnol. Bioeng. Symp.*, 11:555 (1981)], dialysis fermentation [Margaritis et al., *Biotechnol. Bioeng.*, 20:709 and 727 (1978); Kyung et al., *Biotechnol Bioeng.*, 26:252 (1984)] fermentations with a second liquid phase [Wang, 1981, supra; Murphy, Process Biochem., Nov./Dec., 1982, p. 6: Minier et al, *Biotechnol. Bioeng.*, 24:1565 (1982); Hahn-Hagerdal et al., *Biotechnol. Bioeng. Symp.*, 11:651 (1981); Matsumura et al., 3rd *Europ. Cong. Biotechnol.*, 2:415, Topic C5; Pye et al., U. Penn., Interim U.S.D.O.E. Report, June-Aug. 1979]. These reactor adaptations have not proved to be attractive because the resulting economics and/or energy costs have not been competitive.

Among these alternatives the liquid-liquid extraction process has been reported to be the cheapest [Pye, supra]. Even this process has met with limited success, largely because the choice of solvents has been severely limited by cell toxicity. The best solvents have high distribution coefficients, high separation factors, low solubility in water, and high potential for the easy separation of ethanol from the solvent Roddy, *Ind. Eng. Chem. Process Des. Dev.*, 20:104 (1981), has reported that tri-normal-butylphosphate (TBP) is probably the best solvent for ethanol recovery when cell toxicity is not a factor. Murphy et al, supra have attempted to use TBP but found TBP to be partially toxic to the fermentation. Thus Slapack et al., "Thermophilic Bacteria and Thermotolerant Yeasts for Ethanol Production," CRC Press, Inc., Boca Raton, Fl. (1985) have concluded that "solvent extraction does not appear to be a feasible alternative at present since solvents which give good ethanol separation are more toxic to the cell".

The present invention, in contrast, describes a multi-membrane bioreactor system which can employ a toxic solvent for example TBP, in which the rate and extent of the fermentation are significantly increased. This reactor scheme provides evidence for the hypothesis that TBP is not toxic in the dissolved form and that the partial toxicity observed by other investigators is due to droplets of emulsified solvent. The membrane reactor system coupled with correct pressure control protects the cells.

The reactor employed in the process of this invention is described in copending patent application Ser. No. 512,802, filed July 11, 1983, entitled "Continuous Biological Reactor" (which application is hereby incorporated by reference) and comprises a continuous biological reactor including at least four layers comprising: (a) a biocatalyst layer comprising a biocatalyst and a biological product formed by interaction between said biocatalyst and a substrate; (b) a substrate layer comprising said substrate and said biological product; (c) a gaseous layer comprising one or more gaseous nutrients and one or more gaseous byproducts; and (d) a product layer comprising said biological product and extractant; wherein (a) and (b) are separated from each other by means of a first membrane which is permeable to said substrate and said biological product and impermeable to said biocatalyst; wherein (c) is separated from one of (a) or (b) by a second membrane which is permeable to said gaseous nutrients and said gaseous by products and impermeable to liquids; and wherein (d) is separated from the other of (a) or (b) by a third immobilized liquid membrane which absorbs said biological product and promotes diffusion of the product into (d); whereby the biocatalyst and substrate interact to produce the biological product, while the biological product is removed from the substrate, thereby recovering said product and preventing said product from accumulating to high concentrations in the substrate or cell layers.

A presentation by the inventors at the Engineering Foundation Conference in January 1984 generally suggests the membrane moderated biological reactors for the production of ethanol.

DESCRIPTION OF THE INVENTION

It has now been discovered that when an immobilized liquid membrane is employed as a product separation means in a biological reactor, even though the liquid in the membrane is toxic or inhibitory toward the biological reaction and is in apparent contact with the cell layer, the reaction proceeds with minimal toxic effect from the solvent. This effect is exemplified in a system for the biological production of ethanol using tri-normal-butylphosphate (TBP) as the product recovery solvent.

The process of the invention is particularly useful in systems where toxicity is caused by the solvent in emulsified form, as the process of the invention prevents or retards emulsification.

Immobilized liquid membranes are well known in the art; see for example U.S. Pat. Nos. 3,335,545 and 3,864,418, as well as "Membranes Separation Process" Meares, ed. Elsevier Scientific Pub. Co., 1976, pp. 321–322; "Recent Developments in Separation Science", Vol. I, L:, ed., CRC Press, 1972, pp. 153–161 and Matson et al., Chem. Eng. Sci., 38:503–524. Since the biological systems are essentially aqueous the membranes in which the solvent is retained should be hydrophobic and the organic solvent employed should be substantially water immiscible.

Figure 1:
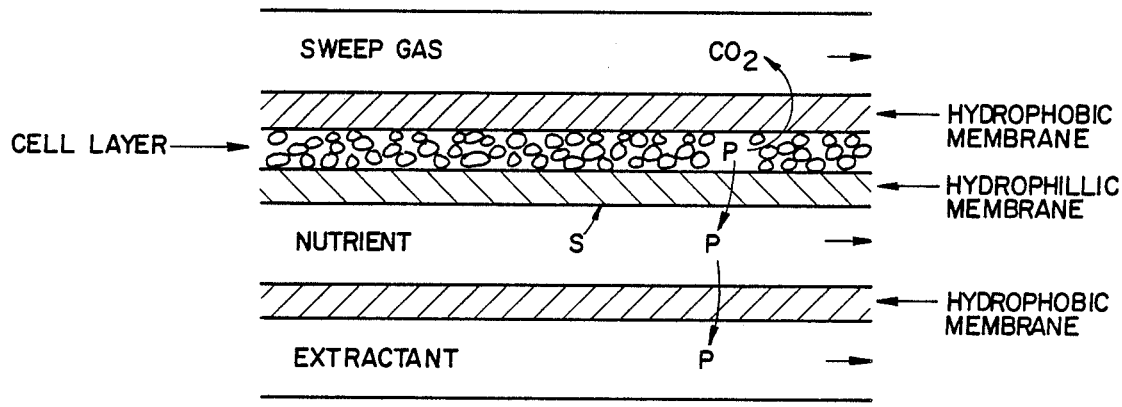
FIG. 1 is a schematic diagram of the basic multimembrane unit. In the system considered S is glucose and P is ethanol.

A multimembrane designed for bioreactions that produce gas and an inhibitory product is depicted in FIG. 1. The membranes provide compartmentalization and organization.

The hydrophobic membrane separating the gas phase from the cells promotes removal of $CO_2$ from cell layer. The hydrophobic nature of the membrane allows passage of the gas while blocking the flow of liquid with high surface tension. Since one mole of $CO_2$ is evolved for each mole of ethanol formed, high reaction rates result in more production of $CO_2$ than can be dissolved in water. Excess $CO_2$ enters the gas phase and if not removed sufficiently rapidly the evolved gas will burst the membranes or create a higher pressure on the cell layer side than in the nutrient layer and exclude water and soluble nutrients from the cell layer.

A hydrophilic membrane is used to separate the cell layer from the nutrient solution. The cells are present in high concentration to achieve a high catalytic density. The cell layer can, in principle, be slowly recirculated if catalyst regeneration is necessary. Unlike other forms of entrapment or adsorption, the membrane will completely retain the cells if the membrane pore size is sufficiently smaller than cell size. Nutrient is supplied to the cells by a combination of diffusion and pressure driven flows.

A hydrophobic immobilized membrane is used to separate the aqueous nutrient phase from an organic solvent. The purpose of the solvent is to selectively absorb the reactor product while rejecting the substrate. Removal of an inhibitory product can greatly increase reaction rate and potentially significantly reduce recovery costs. However, if the solvent itself is toxic or inhibitory toward the reaction it could be expected that, being in contact with the cell layer, it could display a serious adverse effect. In the immobilized liquid membrane, the organic solvent easily wets the membrane while the aqueous phase cannot enter the pores unless a critical entry pressure is exceeded. By maintaining the pressure in the nutrient side higher than in the organic phase, but lower than the critical entry pressure, the solvent is effectively entrapped within the pores. As a consequence cocurrent rather than countercurrent flow may be required to obtain the appropriate pressure drop throughout a long reactor. If the pressure on the solvent side was higher than the nutrient side, or if no membrane was used the solvent and fermentation broth would form a stable emulsion. Such an emulsion is undesirable in terms of product recovery, and, as is demonstrated hereinafter, droplets of the emulsified solvent can interact with the cell envelope resulting in decreased metabolic activity.

The hydrophobic solvent containing immobilized liquid membrane should have had a aqueous phase critical entry pressure higher than the pressure required to deliver nutrients into the cell layer.

The selection of a particular membrane material and solvent is dependent on the biological reaction being conducted. First, the solvent being selected as a solvent for the product of the biological reaction, and second, the membrane material being selected such that it is both hydrophobic and easily wetted by the solvent and so that the solvent impregnated membrane displays the desired critical aqueous phase entry pressure. Generally the method of the invention comprises a method of separating biological product from the cell layer of a membrane-moderated biological reaction using an organic solvent which is normally toxic toward the biological reaction when in contact with product producing cells in the cell layer, which method comprises: separating said product from the cell layer by means of a hydrophobic immobilized liquid membrane which contains said toxic organic solvent and which is adapted to absorb said product and diffuse it from the cell layer thereby recovering said product and preventing said product from accumulating to high concentrations in the cell layer while reducing the toxic effect of the solvent on the cell layer compared to direct cell layer/solvent contact.

EXAMPLES

The following demonstrates the successful extractive fermentation using a practical solvent, e.g. TBP.

Organism: *Saccharomyces cerevisiae* ATCC #24858 (American Type Culture Collection, Rockville, Md.) was maintained on slopes of YM agar at 4° C. and used for all the experiments. The organism was transferred to fresh media every three months.

Media: The inoculum propagation medium composition was: glucose 20 g; yeast extract, 6.40 g; $(NH_4)_2SO_4$ 4.80 g; $KH_2PO_4$, 0.75 g; $MgSO_4.7H_2O$, 0.24 g; $CaCl_2.2H_2O$, 0.036 g; antifoam (food grade C emulsion, Dow Corning) 200 mg; distilled-deionized water, 1 l.

The fermentation medium composition for suspension culture fermentation was: glucose, 100 g: yeast extract, 2 g; $(NH_4)_2SO_4$, 1.5 g; $KH_2PO_4$, 1.5 g; $MgSO_4.7H_2O$, 0.125 g; $CaCl_2.2H_2O$, 0.125 g; antifoam, 200 mg; distilled-deionized water, 1 l. When 150 (g/l) glucose is used, all other nutrients were increased by the same proportion as glucose except antifoam.

The concentrated nutrient solution for addition to suspension culture fermentation was prepared as: yeast extract, 120 g; $(NH_4)_2SO_4$, 90 g; $KH_2PO_4$, 90 g; $MgSO_4.7H_2O$, 7.5 g; $CaCl_2.2H_2O$, 7.5 g; dissolved in 300 ml distilled-deionized water. Volumes of 10 or 5 ml of the above concentrated nutrient medium in test tubes were sterilized for 5 minutes at 121° C.

The normal nutrient solution for addition to suspension culture fermentation had a composition as: yeast extract, 3 g; $(NH_4)_2SO_4$, 2.25 g; $KH_2PO_4$, 2.25 g; $MgSO_4.7H_2O$, 0.188 g; $CaCl_2.2H_2O$, 0.188 g; distilled-deionized water 1 l.

The concentrated nutrients solution for addition to the multimembrane reactor was prepared with the following composition: yeast extract, 180 g; $(NH_4)_2SO_4$, 135 g; $KH_2PO_4$, 135 g; $MgSO_4.7H_2O$, 11.25 g: $CaCl_2.2H_2O$, 11.23 g; distilled-deionized water 1 l. The pH (for all the medium and nutrient solutions) was adjusted to 4.0±0.1 prior to sterilization.

Tributyl phosphate was obtained at 99% purity from Aldrich Chemical Co.

Assays: Glucose was analyzed by an enzymatic method (Calbiochem-Behring S.V.R ™ glucose test kit). The minimum value of glucose concentration that can be measured is 2 mg/l with minor modifications. Reproducibility is ±3.3%.

Ethanol was also analyzed by an enzymatic method (Sigma Chemical Co., No. 322-UV EtOH Assay Kit). The assay of ethanol in TBP was also done by the same enzymatic methods because the presence of TBP did not affect the assay. Minimum detectable concentration was about 2 mg/l and the typical reproducibility was ±2.3%.

Inoculum Propagation: 250 ml inoculum propagation medium in 1 l Bellco flask was inoculated from slope culture of YM agar medium and incubated at 30°±1° C. and 300 rpm for 20 hours and then used as inoculum.

Shake Flask Experiments: To investigate the influence of TBP on the fermentation 100 ml of medium (with 150 g/l glucose) was added to each of six 250 ml Bellco flasks. 1.65 ml TBP (1% (V/V) TBP) was added to each of 2 of the above 6 flasks. 8.25 ml TBP (5% (V/V) TBP) was added to each of 2 of the above 6 flasks. One of the two remaining flasks was used as a control for the addition of the normal nutrient solution while the other was used as a control for the addition of the concentrated nutrient solution. At the beginning, three 10 ml aliquots of concentrated nutrient solution were added to one of each pair of shake flasks and three 10 ml aliquots of normal nutrient solution were added aseptically to the other flask of each pair. All the fermentation media were inoculated with 10 ml inoculum. Fermentation occurred at 30°±1° C. and 150 rpm. Periodically, 5 ml samples were taken, and 5 ml concentrated nutrient solution or 5 ml normal nutrient solution were added. The 5 ml samples were pipetted into sterilize screwcapped vials and preserved at −26° C. for future analysis.

A similar shake flask study was used to investigate the effect of dissolved TBP on the ethanol fermentation. Aliquots of 0.04 ml (0.036% (V/V)) and 0.05 ml (0.045% (V/V)) were added aseptically to 100 ml fermentation medium (with 100 g/l glucose) in 250 ml Bellco flasks. Again a 10 ml inoculum (10% (V/V)) was added aseptically to each flask and fermented at 30°±1° C. and 150 rpm with control. Samples (3 ml) were taken periodically and preserved in the same manner described previously.

Reactor Description: For ease of construction a flat plate type of reactor was chosen. This configuration allows one to directly sample the cell layer and also to insure its initial homogeneous distribution. By controlling the height of the cell chamber frame it is potentially possible to determine the effects of the depth of the cell layer on system response. Reactors with hollow fibers or spiral wound configurations would likely be more suitable for commercial applications.

Figure 2:
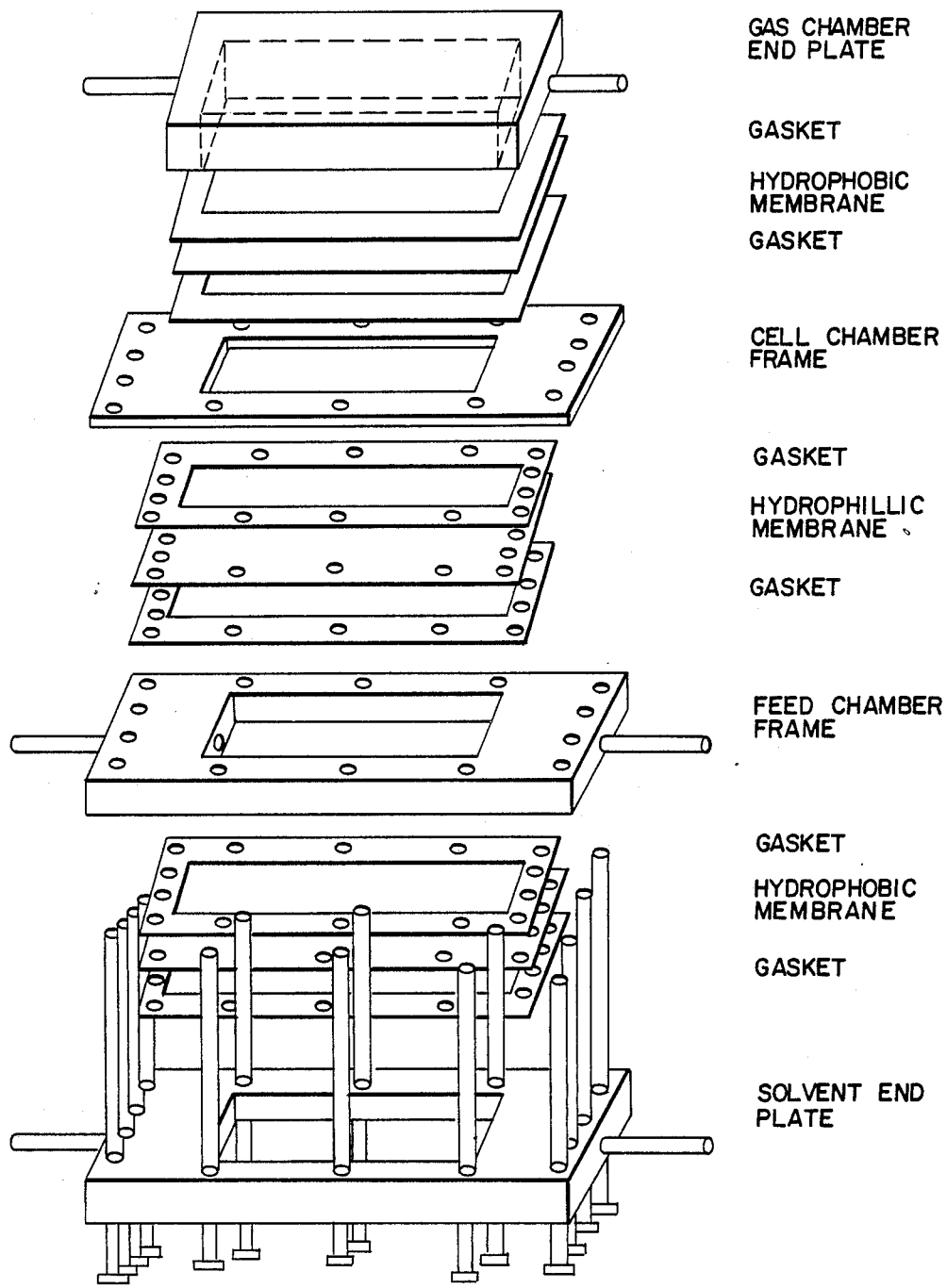
FIG. 2 provides details of construction of the reactor. The cell chamber is 2 mm thick. The overall dimensions are approximately 30.5 cm × 12.5 cm. The inner dimensions (i.e. exposed membrane area) are 6.4 cm×24.4 cm. The gas chamber end plate is 28 cm×9.9 cm. All construction was stainless steel. All gaskets were teflon.

A diagram of the experimental unit is given in FIG. 2. In this system microporous polypropylene membranes made from food grade polypropylene were used. All of these membranes were obtained as flat sheets from the Celanese Corp (Summit, N.J.). Except for the membranes and gaskets all components were machined from stainless steel. Holes were provided so that bolts can be used to align the structure. The system was held together with ten clamps. The reactor was autoclaved for 15 minutes at 121° C. Cells were loaded to the cell chamber by pumping through the end tube of cell chamber frame or by aseptically pipetting the inoculum directly to cell chamber.

The membrane between the gas chamber and cell chamber was Celgard 4410 which is a gas-permeable, water-repellant, heat-embossed hydrophobic laminate of Celgard 2400 bonded to a non-woven polypropylene web and is used as a vent in batteries. The normal thickness of Celgard 4410 is $1.3 \times 10^{-1}$ mm, and the porosity, effective pore size, and flow rate of air at 1 bar are 38%, 0.02 μm and 75 $cm^3 \cdot cm^{-2} \cdot min^{-1}$ respectively. The $CO_2$ produced in the cell chamber was removed through this membrane to the gas chamber.

The membrane between the cell chamber and feed chamber was Celgard 5511 which is a water-wettable, heat-embossed hydrophilic laminate of Celgard 2500 and a polypropylene web and is used in sterile packaging. The normal thickness (dry and wet), porosity, effective pore size, and flow rate of water at 1 bar are $1.3\times10^{-1}$ mm, 45%, 0.04 μm, 0.5 $cm^3 \cdot cm^{-2} \cdot min^{-1}$, respectively.

To extract the ethanol selectively from the aqueous feed media, an immobilized-liquid-membrane concept was applied and K-442 was used as a matrix to immobilize solvent inside the pores of membrane. Celgard K-442 is a developmental, water-repellent, heat-embossed sandwich composite of Celgard 2400 between two polypropylene webs to provide additional mechanical strength.

Figure 3:
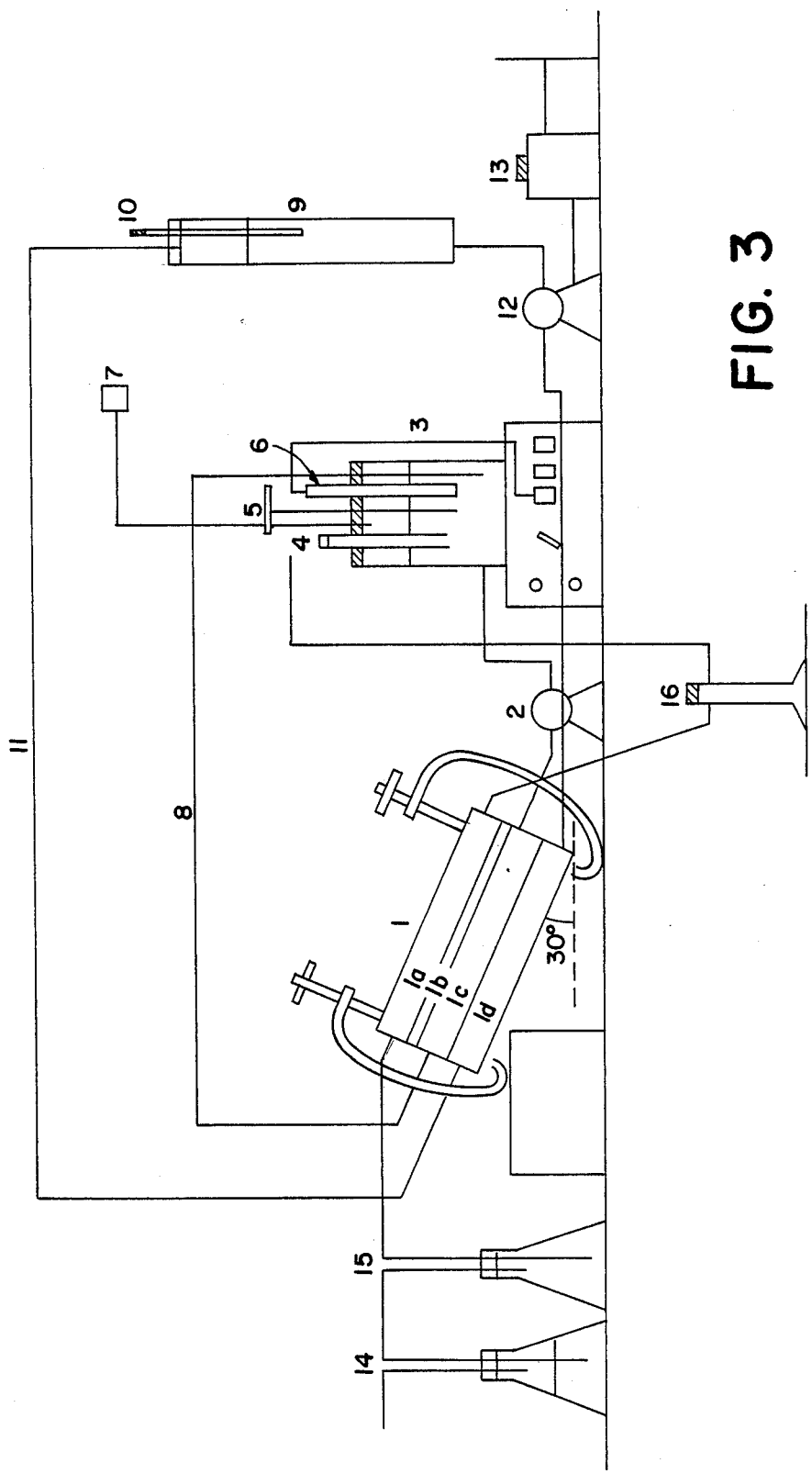
FIG. 3 is a schematic diagram of the system. The numbers refer to: 1, multimembrane reactor; (1a, gas chamber; 1b, cell chamber; 1c, nutrient chamber; 1d, solvent chamber); 2, centrifugal pump; 3, nutrient recycle chamber, 4, sampling port; 5, thermometer; 6, heater; 7, Bolton DFU; 8, silicone tube; 9, TBP recycle cylinder; 10, sampling port; 11, silicone tube; 12, centrifugal pump; 13, powerstat; 14, water trap; 15, trap; and 16, mass cylinder.

Reactor System: For these the system was operated in a batch fluid recycle mode. The system is depicted in FIG. 3.

Preliminary experiments demonstrated that $CO_2$ evolution would cause premature termination of the reaction when no gas permeable membrane was used. The introduction of the gas membrane eliminated much of this problem, particularly when a sweep gas was used. However, prevaporation of the ethanol into a sweep gas stream makes yield calculations difficult thus, inclining the reactor at a 30° angle prevented accumulation of gas pockets in the nutrient chamber and sufficient gas venting was achieved to make a sweep gas stream unnecessary and gas flow by natural convention was satisfactory.

A stirred reservoir of 1.0 L was used. The temperature was controlled using an electrical resistance heater. The recycle vessel provided an opportunity for gassing or degassing.

Separate laboratory-scale centrifugal pumps (Iwaki Magnet Pump, Iwaki Co., Ltd.) were used for recirculation of nutrient and solvent. By varying the voltage to the pump, and consequently pump speed, the pressure of the nutrient stream was 1.9~2.1 psig and 1.10~1.15 psig for the solvent stream Reactor Operation: Both reactors, with and without TBP recirculation, were inoculated by removing clamps, the gas chamber end frame, and the gas/liquid membrane aseptically (see FIG. 2). A 50 ml inoculum was transferred from an inoculum flask by pipetting. The end frame and membrane were returned to position and clamped together Identical 900 ml aliquots of medium were put into both recycle chambers-control and extractive fermentation. Recirculation by a centrifugal pump (Iwaki Magnet pump) was started immediately. Temperature was controlled at 35°±1° C. 30 ml of a concentrated nutrient solution have been added to both reactors at the same time whenever any additions are indicated. The TBP was presaturated with water by mixing 65 ml distilled water with 1 L TBP. 650 ml of water-saturated TBP prewarmed to 35° C. was used during start up. After a predetermined period the TBP has been withdrawn and 650 ml of fresh water-saturated TBP prewarmed to 35° C. has been added.

Figure 4:
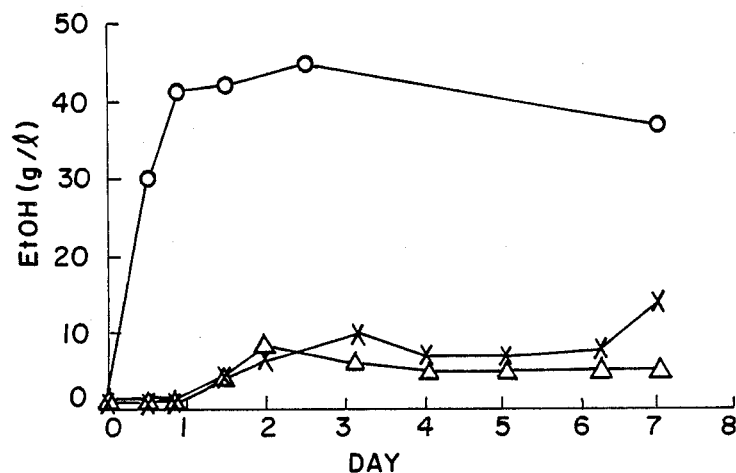
FIG. 4 graphically presents the effect of excess TBP on the ethanol fermentation is shown. The control is depicted by —O—; 1% (v/v) TBP by X—X; 5% (v/v) TBP by Δ—Δ.
Figure 5:
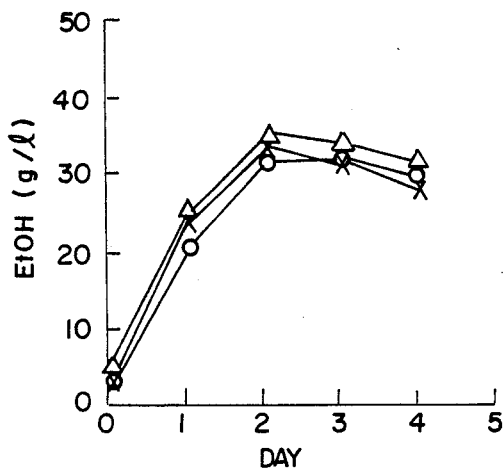
FIG. 5 graphically presents the effect of dissolved. The control is depicted by O—O; 0.036% (v/v) by X—X; 0.045% (v/v) by Δ—Δ.

Suspension Culture Fermentation: A hypothesis tested in these Examples is that the compartmentation in the multimembrane reactor will result in physiological states not accessible in a well mixed system with the same components. The appropriate controls to test this hypothesis are suspended cell, well-mixed batch reactors. Flasks with 1% (V/V) and 5% (V/V) TBP were used because these volumes are far above the saturation point of TBP and enough to give an observable separate layer of TBP. The presence of these levels of TBP had a significant toxic effect on ethanol fermentation (FIG. 4). Although the toxic effect did not completely stop ethanol fermentation, the extent and rate of ethanol fermentation were servely inhibited. It appeared that this inhibition might be due (i) to dissolved TBP, (ii) to the depletion of nutrients in an aqueous media caused by extraction of nutrients from an aqueous media by TBP, and/or (iii) to the physical interaction of droplets of TBP in water with yeast cells. The density of TBP is about 0.97 g/ml. Thus the volume ratio of saturated TBP to water is 0.04% (V/V). Dissolved TBP near the saturation point (0.036% (V/V) and 0.045% (V/V) did not have any toxic effect on ethyl alcohol fermentation (FIG. 5) or on yield of ethanol (Table 1) which indicates that the dissolved TBP does not have any inhibitory effect on the energy metabolism of Saccharomyces cerevisiae.

TABLE 1

| Effect of dissolved TBP near its saturation concentration on ethanol yield. | |
|---|---|
| Fermentation | EtOH Yield |
| Control | 85 ± 7% |
| 0.036% TBP (v/v) | 85 ± 5% |
| 0.045% TBP (v/v) | 85 ± 5% |

*The % is based on the theoretical maximum amount of ethanol produced per glucose consumed. These experiments were performed in shake flasks.

Figure 6:
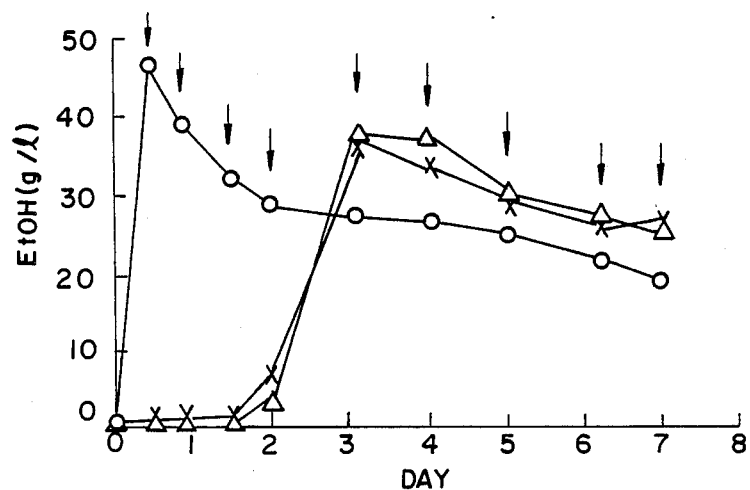
FIG. 6 graphically presents the effects of excess TBP and concentrated nutrient supplements are shown. The control is depicted by O—O; 1% (v/v) TBP by X—X; and 5% (v/v) TBP by Δ—Δ. The arrows indicate the times at which concentrated nutrients have been added.

Concentrated nutrient solutions have been added once a day (after sampling) to 1% (V/V) and 5% (V/V) TBP fermentation media to compensate for the nutrients that might be extracted by a separate TBP phase during ethanol fermentation. As it is shown in FIG. 6, although the extent and rate of ethyl alcohol fermentation were partly resumed, ethanol fermentation was still inhibited significantly. When the fermentation broths with TBP around saturation points (0.036% (V/V) and 0.045% (V/V) were examined microscopically (×1455) after staining with methylene blue, the fermentation broths did not show any emulsion with TBP. Compared to these experiments fermentation broth samples from flasks with 1% (V/V) and 5% (V/V) TBP looked turbid; a high level of TBP droplets emulsified in the fermentation broth were observable under the microscope. Some yeast cells had distinguishable, refractile TBP layers around them. Consequently, it was hypothesized that the dissolved TBP molecules do not have any direct toxic effect, but, instead, the interaction of TBP emulsions with yeast cells results in weakening the cell envelope and/or blocking transport of nutrients. This toxic effect could be termed as physical toxicity in contrast to a chemical toxicity by dissolved molecules.

Multimembrane Bioreactor Performance: The experimental performance test on the multimembrane bioreactor not only was a proof-of-concept, but also gave evidence to support the physical toxicity theory of the effect of TBP on ethanol fermentation by Saccharomyces cerevisiae. To demonstrate the performance of multimembrane bioreactor extractive fermentation system clearly the experiments were designed to maintain all the conditions—inoculum, temperature, media, etc.—same as the control system except for the addition of a TBP chamber.

Figure 7:
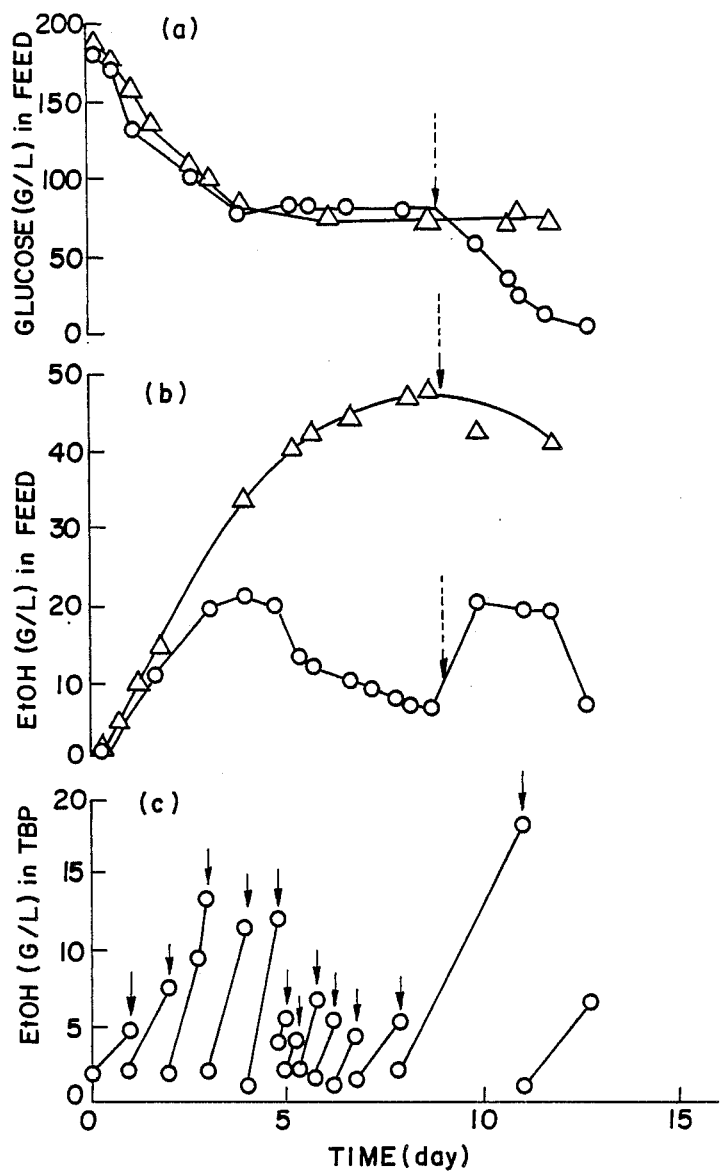
FIG. 7 graphically presents a comparison of the multimembrane bioreactor system with TBP to a control without a solvent layer is shown. Solid arrows indicate time points of addition of fresh TBP and removal of "used" TBP. The dashed arrow indicates the time of addition of concentrated nutrient. The extractive fermentation (i.e. with TBP) is depicted by O—O while the fermentation only system is depicted with Δ—Δ.

As it is shown in FIG. 7, TBP extraction of ethanol through immobilized-TBP-membrane effectively lowered the ethanol concentration in the recirculating nutrient stream of the extractive fermentation system compared to the control. The glucose consumption rate (ethanol production rate) was faster than the control for about one day at the beginning of fermentation, but it slowed down and stopped at about the fourth day. Thereafter, although ethanol concentration in the nutrient stream of the extractive fermentation was lowered significantly due to TBP extraction there was no change in glucose consumption and ethanol production rate. It was speculated that glucose consumption (ethanol production) was inhibited by nutrient depletion. All the nutrients except glucose were added to both reactors in the form of concentrated nutrient solution on the ninth day. Ethanol started to be produced again in the unit with TBP and the residual glucose was completely utilized in about four days. However, there was no response in the control likely because the high concentration of ethanol inhibited further fermentation.

Figure 8:
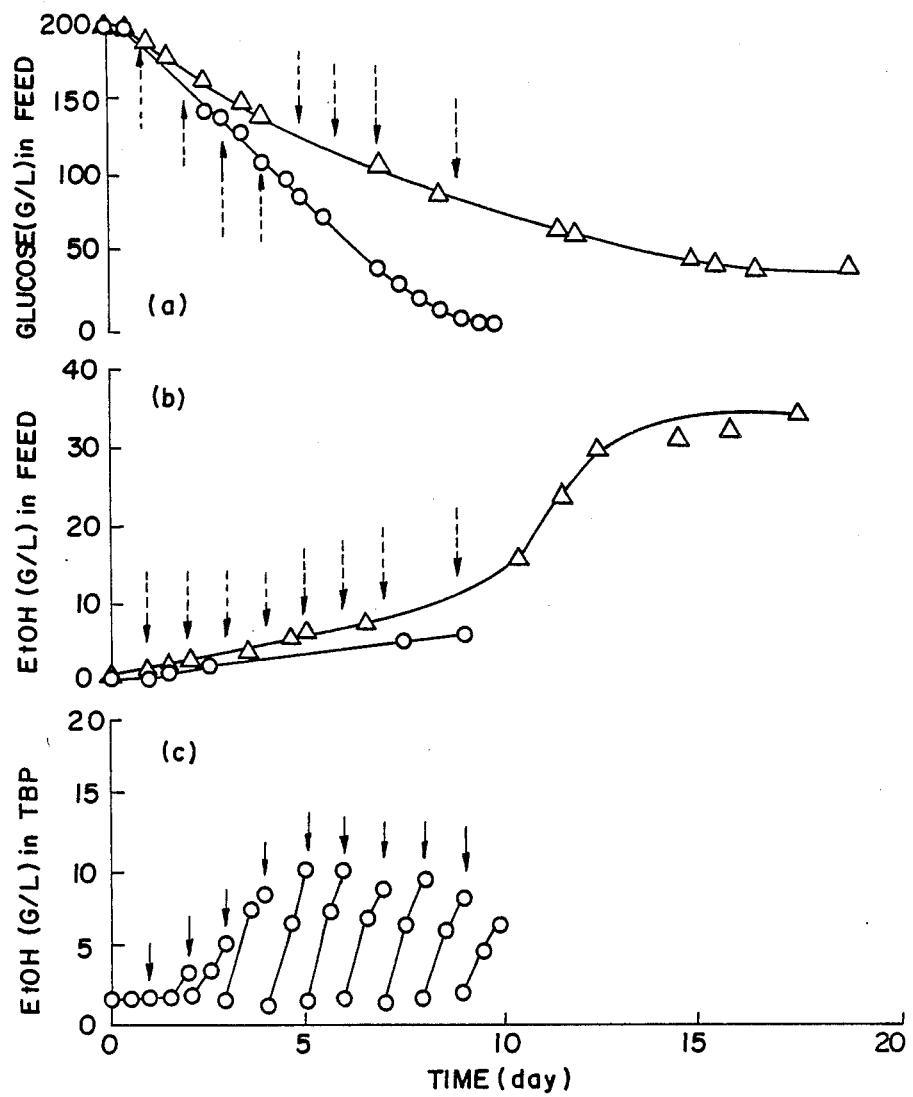
FIG. 8 graphically presents a comparison of the multimembrane bioreactor system with TBP with semicontinuous replenishment of nutrients to a control without solvent extraction is shown. Solid arrows indicate time points of addition of fresh TBP and removal of "used" TBP. The dashed arrow indicates the time of addition of concentrated nutrient. The extractive fermentation (i.e. with TBP) is depicted by O—O while the fermentation only system is depicted with Δ—Δ.

To confirm the role of periodic additions of concentrated nutrient solutions a second experiment was completed. The same concentrated nutrient solutions were added to the fermentation only control and to the extractive system at the same time. FIG. 8 shows the improvement of the rate and extent of ethanol fermentation in the extractive fermentation system compared to the control. When the fermentation medium was observed under microscope, there was no TBP emulsion present. The volume ratio of TBP used to fermentation media used is about 6.4 with 200 (g/l) glucose input, 0 (g/l) glucose output, 6.3 g/l output ethanol concentration in aqueous phase and 5.6 g/l output average ethanol concentration in TBP phase. These results are far better than the extractive fermentation results of Minier et·al. [*Biotechnol. Bioeng.*, 24:1565, 1982 and Advances in Fermentation '83, Chelsea College, London, 1983] who reported 2.55 (Lh$^{-1}$) dodecanol feed flow rate and 0.072 (Lh$^{-1}$) medium feed flow rate with 263 (g/l) glucose input, 0.4 (g/l) glucose output 9.4 (g/l) ethanol concentration in aqueous phase and 3.37 (g/l) ethanol concentration in dodecanol phase. The volumetric flow rate ratio of dodecanol feed to medium feed is about 35.4. Our far superior result is partly due to the successful use of TBP which has better distribution coefficient than dodecanol (0.54 vs. 0.21 at 25° C.) [Parkinson, *Chem. Eng.*, p. 29, June 1, 1981; Roddy, 1981 supra].

The nature of Cellgard K-442 membrane which was used as matrix to immobilize TBP inside the pores of membrane is hydrophobic. The pores of Cellgard K-442 membrane are easily filled with TBP by capillary action. But, the critical entry pressure needed for water to go through the pores of K-442 membrane is high (~3 bars). When the K-442 membrane was contacted with aqueous fermentation broth on one side and with TBP on the other side, membrane pores might have been filled with TBP and, if the pressure inside feed chamber was not maintained somewhat higher than that inside TBP chamber, TBP would flow into the feed chamber. Under these conditions a TBP-fermentation broth emulsion would be created. By maintaining the pressure inside the substrate layer somewhat higher than inside the TBP chamber, but lower than the critical pressure necessary for aqueous fermentation broth to go through K-442 membrane, TBP was completely immobilized inside the pores of K-442 membrane. This correct pressure control on both sides of immobilized-TBP-membrane prevented the flux of TBP into fermentation broth, and, thus, the physical toxicity of TBP on the ethanol fermentation. The extraction of ethanol by TBP immobilized inside the pores of membrane was sufficient to improve the rate and extent of fermentation. These above results provide evidence for the hypothesis that emulsions, not dissolved solvents, are toxic to *S. cerevisiae*. The addition of concentrated nutrient solutions to fermentation broth would not be needed in commercial applications of the multimembrane bioreactor concept because once TBP is saturated with nutrients it will be recycled again to be used as extractant after the ethanol has been removed. The successful use of TBP as immobilized-TBP-membrane in multimembrane bioreactor will give some additional advantages. First of all, and most important, is that the cost and energy necessary for separation of ethanol will be reduced because of a low vapor pressure due to its high boiling point (289° C. at 1 bar). Gas stripping could be used for further concentration of ethanol, or, otherwise simple distillation could be used (see Roddy, 1981, supra). Loss of TBP by emulsification could be prevented and the fermentation broth might possibly be recycled for reuse to reduce process water cost and effluent pollution problems. TBP is readily available and has already been used as industrial solvent.

The Hydrophobic Celgard 4410 membrane was used successfully to remove excess $CO_2$. Preliminary runs demonstrated that without such a membrane the reaction stopped within a few hours; the high gas pressure in the cell layer excluded nutrient. Vigorous gas evolution was observed from the exit of the gas layer. In the extractive fermentation the $CO_2$ gas removal problem was aggravated because of the improved ethanol fermentation rate. At the third day, while active fermentation was occurring after starting the extractive fermentation, it was observed that the recycle line for nutrient has been filled with gas slugs slowing the flow of nutrient. A high capacity centrifugal pump (3500 R.P.M. Cole Parmer) was hooked up with feed line tube to force gas slugs along the feed line to reservoir for degassing. The above high pressure $CO_2$ pockets in the cell chamber forced out some liquid (<15 ml/day) through hydrophobic gas/cell layer membrane. Ultrafiltrate in the gas chamber was collected and returned aseptically to the medium reservoir.

The hydrophilic feed/cell membrane (Celgard 5511) and hydrophobic cell/gas membrane (Celgard 4410) have entrapped yeast cells completely during operation for at least 19 days. This complete retention of cells eliminates cell separation costs. Yeast cells grew preferentially on the surface of hydrophilic cell/feed membrane and the cell layer depth was about 730±50 μm. The cell density of this layer was estimated to be approximately 200±10 (g/L).

It has often been suggested that the bottleneck for progress of extractive fermentation of ethanol is that the better the solvent from separation process point of view, the higher the toxicity to *S. cerevisiae* [Wang, 1981, supra; Murphy et al., supra: Minier et al., supra: Matsumura et al., supra; Pye et al., supra; Roddy, supra]. Roddy, supra has reported that TBP is one of the best solvents to extract ethanol from the separation process point of view if toxicity is not a problem. Previous attempts [Murphy et al., supra; Matsumura et al., supra; Slapack et al, supra] to use TBP in extractive ethyl alcohol fermentation have failed. The multimembrane bioreactor has circumvented some of these problems to give a successful extractive fermentation with a practical solvent.

We claim:

1. A method of separating biological product from the cell layer of a membrane-moderated biological reaction using an organic solvent which is normally toxic toward the biological reaction when in contact with product producing cells in the cell layer which method comprises:

separating said product from the cell layer by means of hydrophobic immobilized liquid membrane which contains said toxic organic solvent and which is adapted to absorb said product thereby recovering said product and preventing said product from accumulating to high concentrations in the cell layer while preventing the toxic solvent from adversely affecting the rate and extent of the biological reaction, said toxic solvent-containing hydrophobic immobilized membrane having a critical aqueous phase entry pressure higher than the pressure employed in the biological reaction to feed aqueous nutrients to said cell layer, and said pressure employed to feed aqueous nutrients to the cell layer being higher than the pressure on the solvent side of the immobilized membrane.

2. A method as in claim 1 wherein the toxic solvent comprises the solvent in the form of an aqueous emulsion.

3. A method as in claim 1 where the cell layer produce ethanol.

4. A method as in claim 3 where use cell layer comprises *Saccharomyces cerevisiae*.

5. A method as in claim 4 where the solvent is tri-normal-butylphosphate.

* * * * *